United States Patent [19]

Sanders et al.

[11] Patent Number: 5,446,212
[45] Date of Patent: Aug. 29, 1995

[54] REDUCED METHYL BROMIDE PROCESS FOR MAKING TETRABROMOBISPHENOL-A

[75] Inventors: Dave C. Sanders, West Lafayette; Arthur G. Mack, Lafayette; Larry D. Timberlake, W. Lafayette, all of Ind.

[73] Assignee: Great Lakes Chemical Corp., West Lafayette, Ind.

[21] Appl. No.: 302,541

[22] Filed: Sep. 8, 1994

[51] Int. Cl.$^6$ .................. C07C 37/62; C07C 39/16
[52] U.S. Cl. .................. 568/726; 568/722; 568/728; 568/776; 568/779
[58] Field of Search ......... 568/776, 779, 726, 722, 568/728, 727

[56] References Cited

U.S. PATENT DOCUMENTS 5,068,463 11/1991 Walter .......................... 568/726
5,237,112 8/1993 LaRose ......................... 568/726

*Primary Examiner*—Werren B. Lone
*Attorney, Agent, or Firm*—Woodard, Emhardt, Naughton, Moriarty & McNett

[57] ABSTRACT

A reduced methyl bromide process for making tetrabromobisphenol A in methanol, including: dissolving bisphenol-A in a methanol solvent to form a bisphenol-A methanol solution, adding bromine to the bisphenol-A methanol solution to brominate bisphenol-A and form tetrabromobisphenol A and hydrogen bromide, exposing the bisphenol-A methanol solution to an amount of a hydrogen peroxide agent to reduce the amount of methyl bromide co-product resulting from the bromination of bisphenol-A in methanol by reducing the amount of hydrogen bromide co-product available to react with the methanol, and collecting the resulting tetrabromobisphenol A product thus formed after the bromination is substantially complete.

20 Claims, No Drawings

REDUCED METHYL BROMIDE PROCESS FOR MAKING TETRABROMOBISPHENOL-A

FIELD OF THE INVENTION

This invention relates generally to processes for making tetrabromobisphenol-A in high yield, productivity and purity with reduced methyl bromide co-production. The invention relates more particularly to reduced methyl bromide processes employing methanol solvents and hydrogen peroxide which result in partial replacement of bromine.

BACKGROUND OF THE INVENTION:

It is well known in the art to prepare tetrabromobisphenol-A (TBBPA) by brominating Bisphenol-A (BPA) in various solvents. Methanol is the solvent of choice because it provides excellent productivity. Additionally, TBBPA recrystallizes from the reaction mixture in high yield with high assay, excellent color, low hydrolyseable bromine and low residual ionic bromides. Another advantage is that the use of a methanol solvent allows product collection by simple filtration.

The major disadvantage of employing a methanol solvent in TBBPA processes is that methyl bromide (MeBr) forms as hydrogen bromide (HBr) liberated from the bromination of BPA reacts with methanol. Methyl bromide was once a desirable by-product which could be collected and sold or used in other industrial processes. However, methyl bromide is now a suspect in the depletion of the ozone. Severe restrictions on the sale of methyl bromide are impending. Therefore, it has become imperative to develop cost-effective manufacturing methods which avoid, or at least reduce, methyl bromide co-production, but maintain product quality and yield.

Approaches to reduce the amount of MeBr co-product in methanol solvent processes for making TBBPA have included the use of aqueous HCl or water and lower reaction temperatures. In such processes, the amount of MeBr produced is reduced because the reaction between HBr and methanol is in an equilibrium that is forced to starting material by adding one of the products, water. Lower temperatures slow down the rate at which equilibrium is obtained. However, in a practical cost effective methanol recovery unit, heat is applied during the distillation and water is removed. This leads to the conversion of HBr into MeBr. Hence, these apparent reductions in MeBr are not valid in processes where methanol is recovered by distillation unless the HBr is neutralized before distillation. This is undesirable because it requires base and further processing steps to recover the valuable bromide ion. It is therefore desirable to actually remove HBr from the reaction medium and not simply dilute it with water or reduce the reaction temperature to slow down MeBr production.

Some processes employ hydrogen peroxide to partially or totally replace bromine during TBBPA production. These processes involve the bromination of BPA in a two phase system including water plus an organic phase. These processes do not employ alcohol solvents and hence alkyl bromide co-production is not a concern. These processes are disadvantageous in that they do not give TBBPA in high yield with the good color and low ionics by simple filtration and washing as the methanol process does.

In spite of these efforts, a need has persisted for methods that exploit the excellent properties of methanol for crystallizing TBBPA while reducing MeBr production even when MeOH recovery by simple distillation is employed. A need has also remained for methods that reduce methyl bromide co-production without expensive changes to current protocols and instrumentation for TBBPA production.

SUMMARY OF THE INVENTION

Briefly describing one aspect of the present invention, there is provided reduced methyl bromide methods for making high yield, high quality tetrabromobisphenol-A using methanol solvents including dissolving bisphenol-A in a methanol solvent to form a bisphenol-A methanol solution, adding bromine to the bisphenol-A methanol solution to brominate bisphenol-A and form tetrabromobisphenol-A and hydrogen bromide, exposing the bisphenol-A methanol solution to an amount of a hydrogen peroxide agent to reduce the amount of methyl bromide co-product resulting from the bromination of bisphenol-A in methanol by reducing the amount of hydrogen bromide co-product available to react with the methanol, and collecting the resulting tetrabromobisphenol-A product thus formed after the bromination is substantially complete.

The present invention is advantageous because it provides the benefits of using a methanol solvent for tetrabromobisphenol-A production without the disadvantage of methyl bromide co-production. The methods of this invention also facilitate efficient use of bromine.

It is an object of the present invention to provide reduced methyl-bromide processes for making tetrabromobisphenol-A.

It is another object of this invention to provide reduced methyl bromide processes which exploit the excellent properties of methanol and simple distillation for making tetrabromobisphenol-A.

It is a further object of the present invention to provide methods for producing tetrabromobisphenol-A in methanol solvents that reduce methyl bromide co-production without costly changes to current industrial protocols and instrumentation for tetrabromobisphenol-A production.

A still further object is to provide methods for producing tetrabromobisphenol-A which include more efficient use of bromine in the bromination of bisphenol-A.

These and other objects, advantages and features are accomplished according to the methods of the following description of the preferred embodiment of the present invention.

DESCRIPTION OF THE PREFERRED EMBODIMENT

For the purposes of promoting an understanding of the principles of the invention, reference will now be made to the preferred embodiments thereof, and specific language will be used to describe the same. It will nevertheless be understood that no limitation of the scope of the invention is thereby intended, such alterations, modifications, and further applications of the principles of the invention being contemplated as would normally occur to one skilled in the art to which the invention relates.

The present invention provides methods for producing high quality TBBPA from BPA with reduced MeBr co-product. MeBr is formed from the bromination of BPA in a methanol solvent. Hydrogen bromide formed from the bromination of BPA reacts with methanol to form methyl bromide and water:

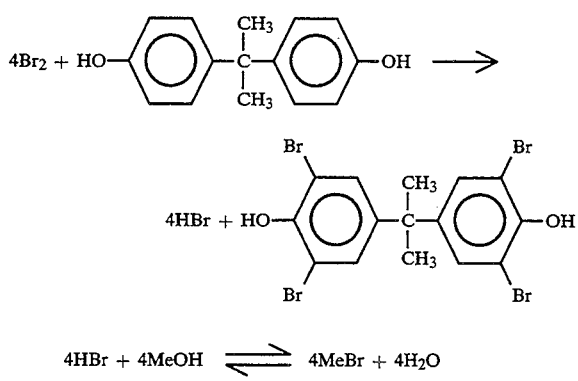

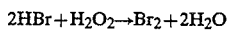

The use of hydrogen peroxide reduces methyl bromide formation and also allows less bromine to be charged to the reactor:

$$2HBr + H_2O_2 \rightarrow Br_2 + 2H_2O$$

The amount of bromine that can be replaced by peroxide has a maximum of 50% which results in 100% reduction in MeBr.

According to methods of the present invention, BPA is dissolved in a methanol solvent to form a BPA-methanol solution. Bromine is added to the BPA-methanol solution to partially brominate BPA and form TBBPA and hydrogen bromide. The bromination reaction temperature is preferably at or below about 40° C. The BPA-methanol solution is exposed to an amount of a hydrogen peroxide agent. Hydrogen peroxide oxidizes hydrogen bromide to bromine, which completes the bromination. This reduces the amount of methyl bromide produced by reducing the amount of hydrogen bromide co-product available to react with methanol. Hydrogen peroxide also allows better utilization of bromine.

Bromine ($Br_2$) may be added to the BPA-methanol solution in an amount which is about the required stoichiometric amount required to make TBBPA, or up to about 4 moles of bromine per mole of bisphenol-A. The methods of the present invention allow the use of less than stoichiometric amounts of bromine. This is advantageous because it tends to reduce the amount of ionic impurity. However, it may be desirable, in some cases, to use a slight excess of bromine so as to increase the yield of TBBPA product.

The BPA-methanol solution is exposed to a hydrogen peroxide agent to reduce the hydrogen bromide co-product available to react with methanol. The BPA-methanol solution is most preferably exposed to the hydrogen peroxide agent after bromine is added to the BPA-methanol solution. It is advantageous to add the agent to the BPA-methanol solution after the BPA is at least partially brominated and an amount of hydrogen bromide has been generated. The amount of hydrogen bromide generated is preferably less than about 20 weight percent. Methyl bromide is not formed in the reaction mixture until the hydrogen bromide concentration reaches approximately 9.0 wt. % in a 40° C. bromination, and approximately 18.0 wt. % hydrogen bromide concentration in a 5° C. bromination.

According to methods of the present invention, the amount of the hydrogen peroxide agent used is preferably equal to the amount required to react with hydrogen bromide resulting from the bromination of bisphenol-A and produce enough bromine to achieve complete bromination. Less than stoichiometric amounts of hydrogen peroxide will result in an incomplete reaction. In practice, increasing the amount of peroxide added to the system lowers the quality of the TBBPA product. This is due to adding water (in the peroxide and formed when HBr reacts with peroxide) prematurely to the reaction while bromination is still occurring. Therefore, it is preferable to use the lowest effective amount of the hydrogen peroxide agent. The highest concentration of hydrogen peroxide available is also preferred over lower concentrations as it contains less water. Currently, 70% hydrogen peroxide is the highest concentration that can be transported. Theoretically, the extra water introduced by the peroxide can be offset by using more methanol in the process. However, this lowers the productivity of the reactor and there is a practical limit.

The BPA-methanol solution is preferably refluxed after the addition of the hydrogen peroxide agent. The purpose of the reflux period is to ensure complete bromination. The term "reflux" refers to conditions whereby the reaction mixture is heated at the boiling point in a vessel equipped with a reflux condenser. The reaction mixture volatilizes, condenses and then drains back into the vessel.

A typical range for productivity that can be achieved with the methods of this invention is 0 to 25% bromine replacement which leads to 0 to 50% reduction in MeBr. This range can of course be extended up to 50% bromine replacement if sufficient methanol is used to offset the water introduced by the hydrogen peroxide. The following are the overall reactions for a 25% replacement of bromine with hydrogen peroxide:

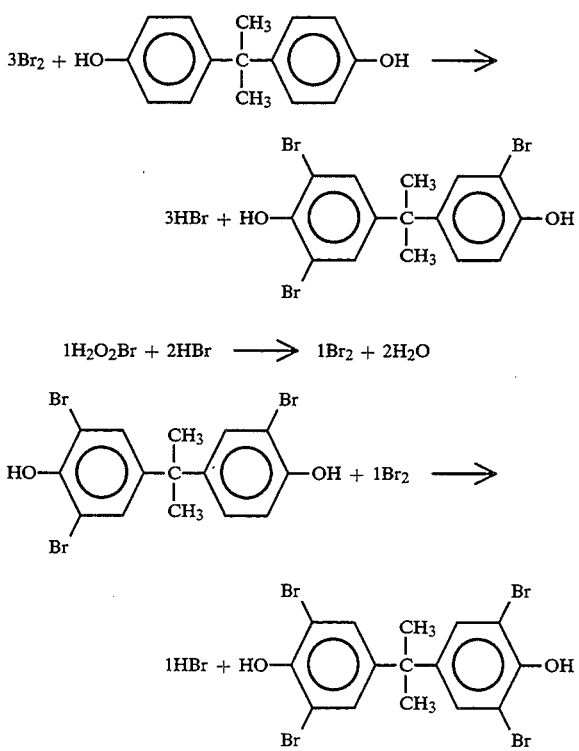

-continued

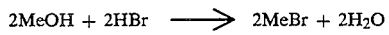
$$2MeOH + 2HBr \longrightarrow 2MeBr + 2H_2O$$

After the bromination is substantially complete the resulting TBBPA product is collected. A further amount of water is preferably added to precipitate the resulting TBBPA after bromination. The precipitated TBBPA can be collected by filtering. The TBBPA product is preferably washed with reducing agents to reduce residual bromine from the TBBPA product. The product is also preferably washed with water to remove ionic materials. The product is then dried and may be tested for APHA solution colors, assay, yield and other characteristics according to methods which are standard in the art.

The methods of the present invention provide dried TBBPA product with APHA solution colors, assay, and residual ionics similar to that produced in methanol solvents without hydrogen peroxide. For example, APHA color values may range from 20 to 40 in acetone and the yield is up to about 99%.

The following specific examples are provided for purposes of illustrating the invention, and no limitations on the invention are intended thereby.

EXAMPLE 1 (COMPARATIVE)

Methanol Process

Bisphenol-A (228 g, 1 mole) was dissolved in methanol (570 ml) at ambient temperature in a vessel equipped with a stirrer, ceramic saddle packed column attached to a condenser and acetone/$CO_2$ trap (for collection of MeBr), thermometer, and cooling bath. Bromine (649g, 4.06 moles) was added with stirring while maintaining the reaction temperature below 40° C. The product partially precipitated at the end of the bromination.

After bromine addition was complete the reaction mixture was quickly heated to reflux (70° C.) and held at reflux for two hours while methyl bromide was collected as a reaction off-gas (3.26 moles). After the hold period, water (100 ml deionized) was added to further precipitate the product and the reaction slurry was cooled to 25° C.

The product was isolated by filtration using a sintered glass filter and aspirator vacuum. The filtrate was set aside for analysis. The cake was plug-flow washed with 70% methanol/30% (200 mls) and water (200 mls deionized) to remove as much of the mother liquor as possible. The cake was slurry washed four times with boiling deionized water (350 mls each) and then dried on a rotary evaporator at 80° C. and 20 mm Hg.

The final product was isolated in 97% yield with a 97% assay of TBBPA. Analysis of the mother liquors showed there was enough HBr present to make another 0.98 moles of MeBr which gives a total MeBr count of 4.1 moles (Theory 4.06).

EXAMPLE 2

Methanol/$H_2O_2$ Process

Bisphenol-A (228 g, 1 mole) was dissolved in methanol (570 ml) at ambient temperature in a vessel equipped with a stirrer, ceramic saddle packed column attached to a condenser and acetone/$CO_2$ trap (for collection of MeBr). Bromine (584g, 3.654 moles) was added with stirring while maintaining the reaction temperature below 42° C.

At the end of the bromine addition, 20 grams of 70% hydrogen peroxide (0.406 moles) was added dropwise while still maintaining the temperature below 40° C.

The reaction mixture was quickly heated to reflux (70° C.) and held at reflux for two hours while methyl bromide was collected as a reaction off-gas (2.44 moles). After the hold period, water (79 mls of deionized) was added to further precipitate the product and the reaction slurry was cooled to 25° C.

The product was isolated by filtration using a sintered glass filter and aspirator vacuum. The cake was plug-flow washed with 70% methanol/30% deionized water (200 ml) and water (200 mls deionized) to remove as much of the mother liquor as possible. The cake was slurry washed four times with boiling deionized water (350 mls each) and then dried on a rotary evaporator at 80° C. and 20 mm Hg.

The final product was isolated in 97% yield and 97% assay. Analysis of the mother liquors showed there was enough HBr present to make another 0.962 moles of MeBr that gives a total MeBr count of 3.4 moles, i.e. a 15% reduction in MeBr over the theoretical value of 4 moles.

EXAMPLE 3 (COMPARATIVE)

Large-Scale Methanol Process

Brominations were carried out in a 3,000 gallon glass lined reactor. Methanol (1650 gallons) and BPA were charged to the reactor. Bromine (15,200 lbs.) was added while the temperature was maintained below 32° C. After bromine addition was complete, the reaction mass was refluxed for 2 hours to complete the bromination. MeBr was formed during this step and was collected as a reaction off-gas. Water (302 gallons) was then added. The product was filtered, washed with water and dried.

TBBPA was obtained as a white powder with an assay of 98.26%, APHA color in acetone of 20, hydrolyseable bromine of 19.6 ppm and ionic bromides of 47.5 ppm.

EXAMPLE 4

Large-Scale Methanol/$H_2O_2$ Process

Brominations were carried out in a 3,000 gallon glass lined reactor. The same charge of BPA and methanol was used as in Example 3, and bromine (13,680 lbs., 10% less) was added while keeping the temperature below 32° C. After bromine addition was complete (100 minutes), 70% peroxide was added from a shot tank above the reactor (462 lbs. of 70% peroxide) in 40 minutes. The reactor temperature was closely monitored when adding the peroxide and kept below 32° C. by cooling and adjusting the rate of peroxide addition (40 minutes). After all the peroxide was charged, the reaction mass was refluxed for 2 hours to complete the bromination. Water (44 gallons) was then added. The product was filtered, washed with water and dried.

TBBPA was obtained as a white powder with an assay of 98.7%, APHA color in acetone of 20, hydrolyseable bromine of 10.4 ppm. and ionic bromides of 29.5 ppm.

While the invention has been described in detail in the foregoing description, the same is to be considered as illustrative and not restrictive in character, it being understood that only the preferred embodiments have been shown and described, and that all changes and modifications that come within the spirit of the invention are desired to be protected.

What is claimed is:

1. A reduced methyl bromide process for making tetrabromobisphenol A in methanol, comprising:
    dissolving bisphenol-A in a methanol solvent to form a bisphenol-A methanol solution;
    adding bromine to the bisphenol-A methanol solution to partially brominate bisphenol-A and form tetrabromobisphenol A and hydrogen bromide;
    exposing the partially brominated bisphenol-A methanol solution to an amount of a hydrogen peroxide agent to reduce the amount of methyl bromide co-product resulting from the bromination of bisphenol-A in methanol by reducing the amount of hydrogen bromide co-product available to react with the methanol; and
    collecting the resulting tetrabromobisphenol A product thus formed after the bromination is substantially complete.

2. The process of claim 1 wherein bromine is added in an amount which is no more than the required stoichiometric bromine required to make tetrabromobisphenol A.

3. The process of claim 2 wherein bromine is added in an amount which is less than the required stoichiometric bromine required to make tetrabromobisphenol A.

4. The process of claim 1 wherein the bromine is added in an amount of no more than about four moles of bromine per mole of bisphenol-A.

5. The process of claim 1 wherein the amount of hydrogen peroxide agent is equal to the amount required to:
    react with hydrogen bromide resulting from the bromination of bisphenol-A, and
    produce enough bromine to achieve complete bromination of the bisphenol-A.

6. The process of claim 1 wherein the hydrogen peroxide agent includes 70% hydrogen peroxide.

7. The process of claim 1 further comprising maintaining a bromination reaction temperature below about 40° C.

8. The process of claim 1, further comprising refluxing the bisphenol-A methanol solution after exposing the bisphenol-A methanol solution to the hydrogen peroxide agent.

9. The process of claim 1 wherein the Bisphenol-A methanol solution is exposed to the hydrogen peroxide agent after bromine is added to the bisphenol-A methanol solution.

10. The process of claim 9 wherein the Bisphenol-A methanol solution is exposed to the hydrogen peroxide agent after the bisphenol-A is at least partially brominated and an amount of hydrogen bromide has been generated.

11. The process of claim 1 wherein the amount of hydrogen bromide is less than about 20 weight percent.

12. The process of claim 11 wherein the amount of hydrogen bromide is about 18 weight percent.

13. The process of claim 11 wherein the amount of hydrogen bromide is about 9 weight percent.

14. The process of claim 1 wherein the collecting includes adding an amount of water to precipitate the resulting tetrabromobisphenol A after the bromination of the bisphenol-A is substantially complete.

15. The process of claim 14 wherein the collecting includes filtering the precipitated tetrabromobisphenol A.

16. The process of claim 1 further comprising washing the tetrabromobisphenol A product with reducing agents to remove residual bromine from the tetrabromobisphenol A product.

17. The process of claim 1 further comprising washing the tetrabromobisphenol A product with water to remove ionic materials.

18. The process of claim 1 further comprising drying the tetrabromobisphenol A product.

19. The process of claim 1 wherein the tetrabromobisphenol A product has an APHA color of 20 to 40 in acetone and up to about 99% yield.

20. The process of claim 19 wherein the tetrabromobisphenol A produce was an APHA color of 20 in acetone.

* * * * *